(12) United States Patent
Martens

(10) Patent No.: US 8,942,446 B2
(45) Date of Patent: Jan. 27, 2015

(54) SYSTEM AND METHOD FOR PLANNING A NEUROSURGICAL OPERATION

(75) Inventor: Hubert Cecile Francois Martens, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 130 days.

(21) Appl. No.: 13/640,490

(22) PCT Filed: Apr. 8, 2011

(86) PCT No.: PCT/IB2011/051525
§ 371 (c)(1),
(2), (4) Date: Oct. 11, 2012

(87) PCT Pub. No.: WO2011/128823
PCT Pub. Date: Oct. 20, 2011

(65) Prior Publication Data
US 2013/0035922 A1    Feb. 7, 2013

(30) Foreign Application Priority Data
Apr. 14, 2010  (EP) ..................................... 10159853

(51) Int. Cl.
G06K 9/00    (2006.01)
G06F 19/00   (2011.01)

(52) U.S. Cl.
CPC ........ *G06F 19/3437* (2013.01); *G06F 19/3481* (2013.01)
USPC ....................................................... 382/128

(58) Field of Classification Search
None
See application file for complete search history.

(56) References Cited

U.S. PATENT DOCUMENTS

| | | |
|---|---|---|
| 2005/0273001 A1 | 12/2005 | Schmainda et al. |
| 2007/0043401 A1 | 2/2007 | John |
| 2012/0265262 A1* | 10/2012 | Osorio ............................. 607/3 |
| 2012/0296569 A1* | 11/2012 | Shahaf et al. ................... 702/19 |

FOREIGN PATENT DOCUMENTS

EP    0945814 A2    9/1999

OTHER PUBLICATIONS

Achard, S., Salvador, R., Whitcher, B., Suckling, J., and Bullmore, E., A Resilient, Low-Frequency, Small-World Human Brain Functional Network with Highly Connected Association Cortical Hubs, 2006, The Journal of Neuroscience, vol. 26, No. 1, pp. 63-72.*

(Continued)

*Primary Examiner* — Stephen R Koziol
*Assistant Examiner* — Jonathan S Lee

(57) ABSTRACT

A system (10) and method (20) for planning a neurosurgical operation are provided the system (10) comprises an input (11) for receiving functional data (25) and anatomical data of a brain region (31), and a processor (12) configured to perform the method (20) according to the invention. The method (20) comprises analyzing (26) the functional data (25) to form a network representation (27) of functional connections, mapping the network representation (27) of the functional connections and the anatomical data to a common coordinate system, determining an expected function loss associated with a simulated removal of network nodes (32) or network connections (42) from the network representation (27), and identifying critical network connections and/or critical network nodes based on the expected function loss.

15 Claims, 5 Drawing Sheets

(56) References Cited

OTHER PUBLICATIONS

Bai, L., Qin, W., Tian, J., Dai, J., and Yang, W., Detection of dynamic brain networks modulated by acupuncture using a graph theory model, 2009, Progress in Natural Science, vol. 19, pp. 827-835.*

Bullmore, E. and Sporns, O., Complex brain networks: graph theoretical analysis of structural and functional systems, 2009, vol. 10, Nature, pp. 186-198.*

Guye, M. Bettus, G., Bartolomei, F., and Cozzone, P.J., Graph theoretical analysis of structural and functional connectivity MRI in normal and pathological brain networks, 2010, Magn Reson Mater Phy, vol. 23, pp. 409-421.*

Salvador, R., Suckling, J., Coleman, M.R., Pickard, J.D., Menon, D., and Bullmore, E., Neurophysiological Architecture of Functional Magnetic Resonance Images of Human Brain, 2005, vol. 15, pp. 1332-1342.*

Wang, J., Zuo, X., and He, Y., Graph-based network analysis of resting-state functional MRI, 2010, Frontiers in systems neuroscience, vol. 4, pp. 1-14.*

Simon K. Warfield, Matthieu Ferrant, Xavier Gallez, Arya Nabavi, Ferenc A. Jolesz and Ron Kikinis. Real-Time Biomechanical Simulation of Volumetric Brain Deformation for Image Guided Neurosurgery. In SC 2000: High Performance Networking and Computing Conference; Nov. 4-10, 2000; Dallas, USA, 230:1-16, 2000.

Dirk Winkler, Gero Strauss, Dirk Lindner, Andreas Richter, Margret Hund Georgiadis, Yves Von Cramon and Jurgen Meixensberger. The Importance of Functional Magnetic Resonance Imaging in Neurosurgical Treatment of Tumors in the Central Region. Clinical Neuroradiology, vol. 15, No. 3/ Sep. 2005, pp. 182-189.

Heiko Lippmann, Frithjof Kruggel. Quasi-real-time neurosurgery support by MRI processing via grid computing. Neurosurgery Clinics of North America, vol. 16, Issue 1, pp. 65-75 (2005).

Bradley K. Weiner, Rikin Pates, Phillip Noble. Randomized trials and registries: a computer simulation to study the impact of surgeon/patient factors on outcomes. The Spine Journal, vol. 8, Issue 6, Nov.-Dec. 2008, pp. 959-967.

A.G. Gallagher, O. Traynor. Simulation in surgery: opportunity or threat? Irish Journal of Medical Science, vol. 177, No. 4/ Dec. 2008, pp. 283-287.

Robert F. Dougherty, Michal Ben-Shachar, Roland Bammer, Alyssa A. Brewer, Brian A. Wandell. Functional organization of human occipital-callosal fiber tracts. proceedings of the National Academy of Sciences. 7350-7355, May 17, 2005, vol. 102, No. 20.

* cited by examiner

SYSTEM AND METHOD FOR PLANNING A NEUROSURGICAL OPERATION

FIELD OF THE INVENTION

This invention relates to a system for planning a neurosurgical operation, the system comprising an input for receiving anatomical data and functional data of a brain region, a processor for mapping the anatomical data and the functional data to a common coordinate system and identifying critical network connections and/or critical network nodes, and an output for providing a visual representation of the anatomical data and the functional. This invention further relates to a method and a computer program product for planning a neurosurgical operation.

BACKGROUND OF THE INVENTION

Brain surgery commonly involves the removal or destruction of suspect regions. For example, for brain tumors surgical resection is often the first treatment of choice. For drug resistant epilepsy, removal or destruction of the epileptic focus by surgical means is an important treatment. Brain surgery does not always involve open surgery, but is nowadays also performed in non-invasive ways of utilizing, e.g., stereotactic radiosurgery. During brain surgery, it is very important not to damage critical structures and connections in the brain. Damaging brain tissue during an operation usually leads to function loss afterwards. The brain has some ability to recover when damaged, but this ability is limited. Minimizing damage made during surgical intervention or radiotherapy is achieved by carefully planning the surgery using pre-operative medical images like MRI.

Often intra-operative visualization (microscope, ultrasound, MR, X-ray) is used to provide imaging information during the procedure. Diffusion-tensor MRI (DTI) based tractography can be considered as a very advanced anatomic imaging modality that visualizes the important white-matter tracts in the brain that connect different brain regions. The registration of all these data to a common framework and the combined visualization of these data provide surgeons with a detailed anatomical map of the brain that supports them in determining an optimal surgical plan.

Today, most advanced brain-surgery planning systems take into account both anatomical image information (contrast-enhanced MRI, CT, etc., that high-light specific brain anatomy) as well as functional image information (fMRI, PET, MEG, EEG, etc., that high-light specific brain function). Functional brain imaging is aimed at characterizing the brain in terms of its physiology, functional architecture and dynamics. Functional imaging can be based on analysis of data acquired using brain imaging modalities such as electro-encephalography (EEG), magneto-encephalography (MEG), functional magnetic resonance imaging (fMRI), or optical techniques such as near-infrared spectroscopy (NIRS).

A neurosurgical planning system visualizing both functional and anatomical data is known from the US patent application published as US 2005/0273001 A1. The system described in that application uses fMRI images, DTI images and perfusion images of the brain and selectively displays them on top of one another. All displayed images are aligned with an anatomical image of the brain. The transparency of each layer can be adjusted. Although such a system has some advantages over systems using only anatomical imaging, there is a need for a smarter and more sophisticated combination of anatomical and functional data in order to allow the surgeon to make a better informed decision and to increase the ability to minimize function loss after the operation.

It is an object of the invention to provide a system and method for planning a neurosurgical operation, which system and method improve the ability to avoid function loss after the operation.

SUMMARY OF THE INVENTION

According to a first aspect of the invention, this object is achieved by providing a system for planning a neurosurgical operation, the system comprising an input, a processor and an output. The input is provided for receiving functional data and anatomical data of a brain region. The processor is configured to analyze the functional data to form a network representation of functional connections, the network representation comprising network nodes and network connections interconnecting the network nodes, to map the network representation of the functional connections and the anatomical data to a common coordinate system, to determine an expected function loss associated with a simulated removal of one of the network nodes or network connections from the network representation, and to identify critical network connections and/or critical network nodes based on the expected function loss. The output is provided for providing a visual representation of the network representation of the functional connections.

This neurosurgical planning system takes into account the functional network properties of the brain in relation to their anatomical substrate. It is an essential feature of brain function that it relies on its network properties, i.e. function is not localized to individual units but arises also from network mediated interactions between units. Recent analysis techniques of functional imaging data are therefore aimed at not only quantifying activity in individual units (e.g. EEG channels or fMRI voxels) but also at quantifying the interactions and correlations between units being representative of the underlying network.

The functional data which, e.g., may be fMRI, EEG, MEG and/or NIRS data is analyzed to form a network representation of functional connections in the brain. The functional data shows relations between mental or physical activities of the patient and neural activity in different parts of the patient's brain. Repeated, simultaneous or correlated activity in different brain regions indicates a functional connection between said regions. By analyzing the functional data, it is possible to identify functional connections and to make a network representation of said connections. The network representation comprises network connections and network nodes. The resulting network can be analyzed geometrically providing e.g. insight in properties like critical nodes ('hubs') having high connectivity to other network parts. The network representation and the anatomical data are mapped to a common coordinate system, making it possible to link removal or damage of a specific brain region to changes in the network representation of the functional connections. Expected function loss following removal or damage of a specific brain area can then be determined using network theory and network analysis techniques. As a result of the network analysis, critical network connections and network nodes are identified and may be avoided in the upcoming neurosurgical operation. Also less critical network connections and network nodes may be identified. When planning a neurosurgical operation it may be decided to apply a more aggressive treatment to the less critical regions.

By, e.g., identifying network connections and/or network nodes critical to neurological recovery, specifically these connections can be spared (conservative treatment) thereby optimizing the potential for post-surgical neurological recovery. Further, by identifying network connections and/or network nodes less critical for recovery (i.e. easily 'rewirable'), more aggressive treatment in those areas can be performed. This planning system will allow for an effective treatment strategy that spares as much as possible the brain's intrinsic ability to recover, learn, and rewire functionality.

The analysis of the received functional data for making the network representation of the functional connections may comprise calculating a pair wise correlation for a plurality of data channels comprised in the functional data.

The expected function loss may, e.g., be determined using a topological network analysis of the network representation. This topological network analysis may, e.g., comprise calculating clustering coefficients of the network nodes and/or path lengths of the network connections.

In a preferred embodiment, the system further comprises planning tools for planning a surgical trajectory avoiding the identified critical network connections and/or critical network nodes.

The planning system preferably comprises an output for providing a visual representation of the network representation of the functional connections. The critical network connections and/or the critical network nodes may be highlighted in the visual presentation. Additionally, an appearance of the network connections and of the network nodes in the visual representation may depend on the expected function loss. The visual representation preferably also shows the anatomic data.

According to a second aspect of the invention, a method is provided comprising receiving functional data and anatomical data of a brain region, analyzing the functional data to form a network representation of functional connections, the network representation comprising network nodes and network connections interconnecting the network nodes, mapping the network representation of the functional connections and the anatomical data to a common coordinate system, determining an expected function loss associated with a simulated removal of one of the network nodes or network connections from the network representation, and based on the expected function loss, identifying critical network connections and/or critical network nodes.

According to a third aspect of the invention, a computer program product is provided for planning a neurosurgical operation. The program is operative to cause a processor to perform the method as described above.

These and other aspects of the invention are apparent from and will be elucidated with reference to the embodiments described hereinafter.

DETAILED DESCRIPTION OF THE EMBODIMENTS

Figure 1:
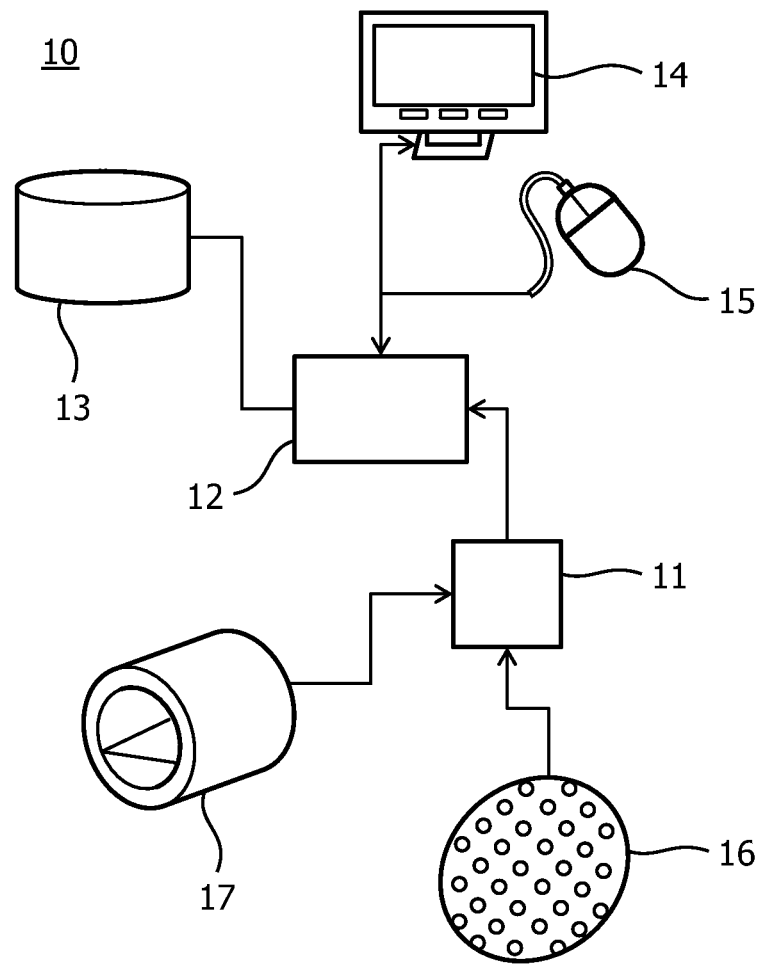
FIG. 1 schematically shows a neurosurgical operation planning system according to the invention, FIG. 2 schematically shows a method for planning a neurosurgical operation, FIG. 3 schematically shows a distribution of functional sensors over a skull of a person to undergo neurosurgical surgery, FIG. 4 visualizes a network analysis of functional data obtained by the sensors of FIG. 3, FIG. 5 visualizes a removal of a network site from the network of FIG. 4, FIG. 6 visualizes a removal of a network connection from the network of FIG. 4.

FIG. 1 schematically shows a neurosurgical operation planning system 10 according to the invention. The system 10 comprises a processor 12 for performing the planning method according to the invention. An input 11 of the processor 12 is coupled to a source of functional data 16 and a source of anatomical data 17. The source of functional data 17 may, e.g., be an fMRI, EEG, MEG and/or NIRS data source. Any type of data linking neuronal activity to brain functions or showing correlation between neuronal activity in different parts of the nervous system may serve as input for the operation planning method according to the invention. Alternatively, earlier obtained functional data may be stored on a storage means 13 coupled to the processor 12. The storage means 13 may, e.g., be a hard disk, solid state memory or optical storage medium. In addition to functional data, the processor 12 also receives anatomical data. The anatomical data may come from anatomical imaging apparatuses 17, such as an MRI or DTI apparatus. Any type of data describing the physical structure of the imaged brain sections may serve as input for the operation planning method according to the invention. The storage medium 13 may comprise earlier obtained anatomical data to be used in the planning method.

The processor 12 combines the functional data and the anatomical data received at the input 11. The combined information is used in a simulation for estimating the effects of possible surgical operations. The results of this simulation and/or estimation may be shown on a display 14 coupled to the processor 12. A keyboard, mouse 15 or other pointing device is provided for allowing user input for initiating or controlling the claimed method and/or for manipulating the output shown on the display screen 14. In the following, it will be described how the functional and anatomical data are combined to provide information about a planned neurosurgical operation and how the results of the planning method may be displayed. Additionally, an exemplary way of providing the functional data needed for the method according to the invention is disclosed.

Figure 2:
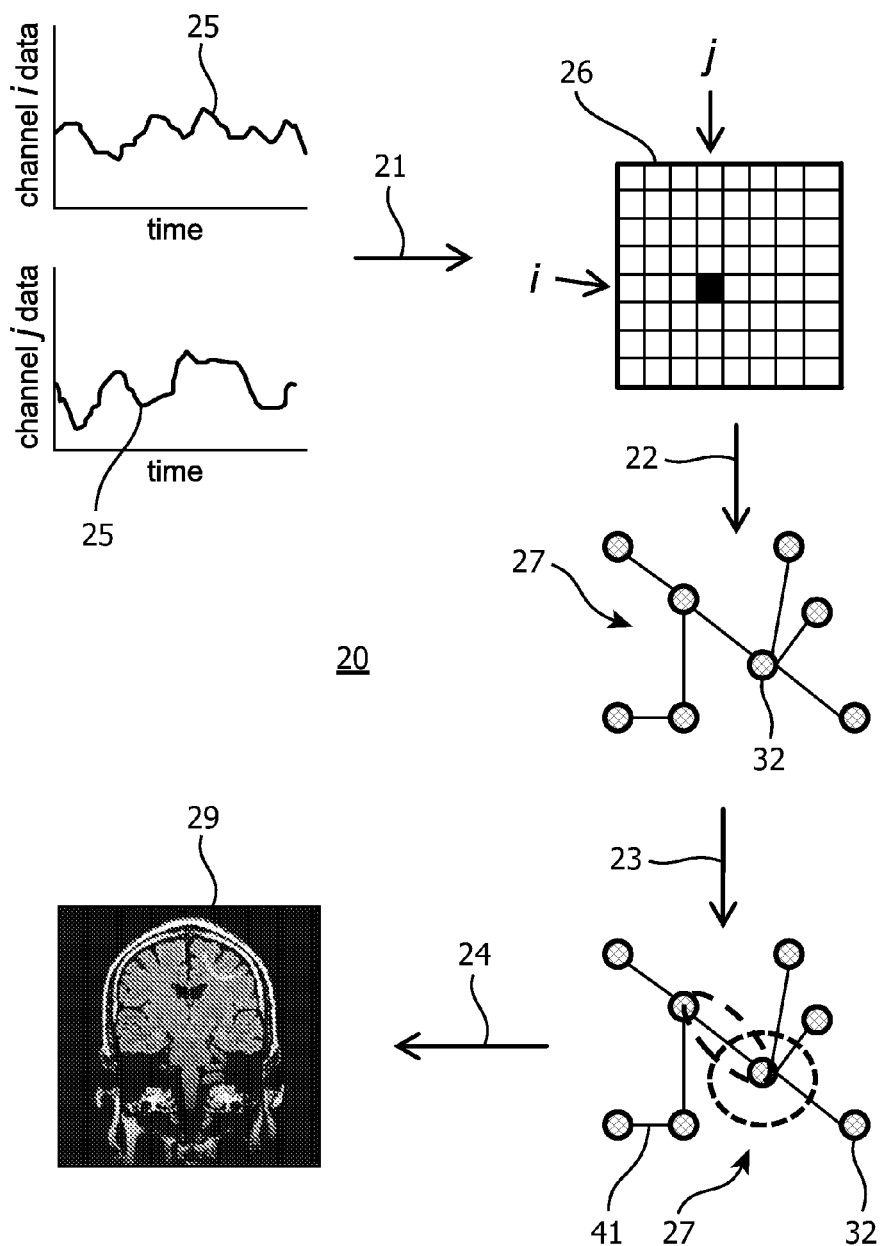

FIG. 2 schematically shows an exemplary method 20 for planning a neurosurgical operation. The method 20 starts with obtaining or receiving functional data. In this example, the functional data comprises at least two channels 25 corresponding to activity in different areas of a human or animal nervous system. The functional data may, e.g., be derived from functional brain imaging data such as fMRI images. Alternatively EEG, MEG and/or NIRS data sources are used for obtaining the functional data. In correlation step 21, a coherence or correlation analysis may be used for determining functional connectivity of different brain areas. The correlation analysis 21 may e.g. calculate a correlation of time-courses of measured functional MEG data channels 25. Correlation coefficients may be organized in a correlation matrix 26, such that at position (i,j) in the matrix 26 the correlation coefficient for the channels 25 i and j is provided. Repeating the correlation calculation for all pairs of data channels 25 results in a complete matrix 26. Instead of correlation coefficients, the correlation matrix 26 may comprise binary values indicating 'correlation' or 'no correlation'.

In network generating step 22, a network 27 of functional connectivity is derived from the calculated correlations. The network 27 comprises network sites 32 representing the respective data channels. Each network site 32 may, e.g., correspond to a position of an EEG sensor or an area of function related neuronal activity in an imaged brain. Correlating network sites 32 are connected by network connections 41. The network 27 thus shows which brain regions are functionally connected to which other brain regions. From the network 27 shown in FIG. 2 it is clear that some network sites 32 are functionally connected to only one other network site 32 and some are connected to more network sites 32.

In network analysis step 23 a topological analysis of the functional connectivity network 27 is made. For this analysis, graph theoretic techniques may be used. For example, a clustering coefficient (connectivity density) or path length (distance measure between network sites 32) may be determined. Critical network sites 32 may be identified as sites 32 having a high clustering coefficient. Additionally, the effects of an intervention may be simulated and quantified in order to identify the relation between a simulated intervention (network modification) and the impact on the functioning of the network 27. The purpose is to identify the more critical network sites 32 and connections 41 that should be spared in an intervention.

In mapping step 24, the functional network 27 is mapped to the patient's anatomy. For the mapping, the functional network 27 and the received anatomical data are mapped to a common coordinate system. Fiber pathways may be found using tractographic techniques. Network connections 41 may be mapped to the detected fiber tracts and network sites 32 to discovered neuronal structures. Combined images 29 may be generated showing the analyzed functional network 27 overlaid on the anatomical information. Color coding or other ways of highlighting may be used for indicating how critical a certain structure or connection is for the functioning of the brain. This will allow a surgeon to make an assessment of how planned interventions may have an impact on brain network functioning.

Figure 3:
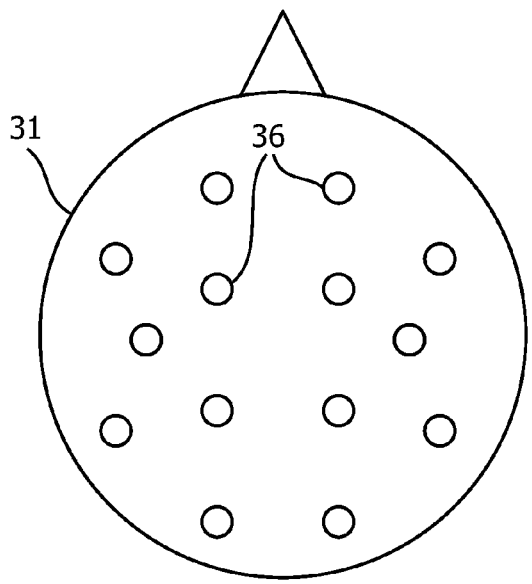

FIG. 3 schematically shows a distribution of functional sensors 36 over a skull 31 of a person to undergo neurosurgical surgery. In this example, the functional data is obtained by 14 EEG sensors 36 distributed over the patient's skull 31. The sensors 36 are arranged for registering neuronal activity in brain areas close to the sensors 36. Each sensor 36 may provide a data channel 25 to be used as input for the method shown in FIG. 2. The data from the channels 25 represents the neuronal activity at neuronal network sites 32 at positions corresponding to the sensor 36 positions. Correlation coefficients indicating the correlation between two of the sensors may be used for making a 14 by 14 correlation matrix 26 as shown in FIG. 2.

Figure 4:
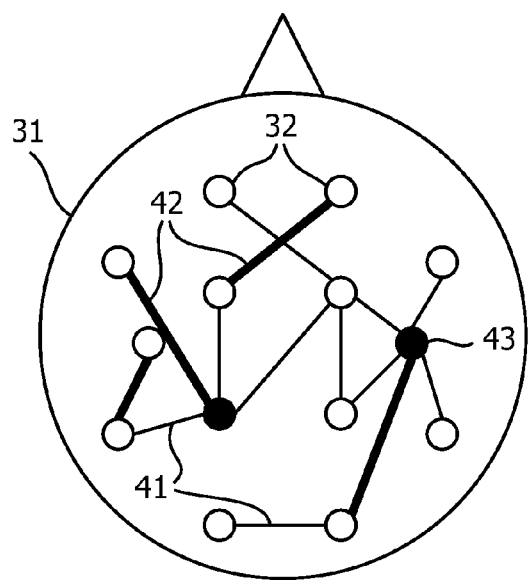

FIG. 4 visualizes the results of a network analysis of functional data obtained by the sensors 36 of FIG. 3. Correlating pairs of network sites 32 are indicated by drawing a connection 41, 42 between the functionally related network sites 32. The more critical connections 42 are distinguished from the less critical connections 41 by using a thicker line to represent the connection 42. Alternatively, color coding or other highlighting techniques may be used for indicating how critical the different connections 41, 42 are. Also for the network sites 32, 43 color coding or other types of highlighting may be used for indicating how critical the network sites 32, 43 are.

Figure 5:
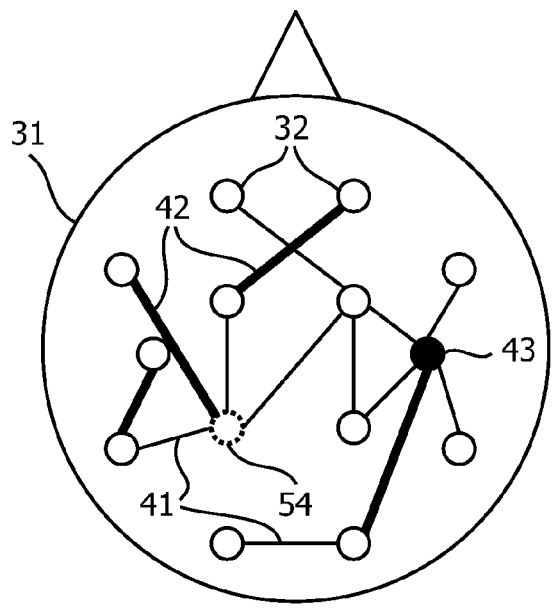

FIG. 5 visualizes a damage or removal of a network site 54 from the network of FIG. 4. The removal is indicated by using a dotted circle representing the network site 54, but may be indicated in different ways. As a result of this removal, other network sites may lose the connection to the functional network. This may cause temporary or permanent function loss. Temporary function loss may be compensated by the intrinsic capability of the brain to rewire damaged neuronal structures.

Figure 6:
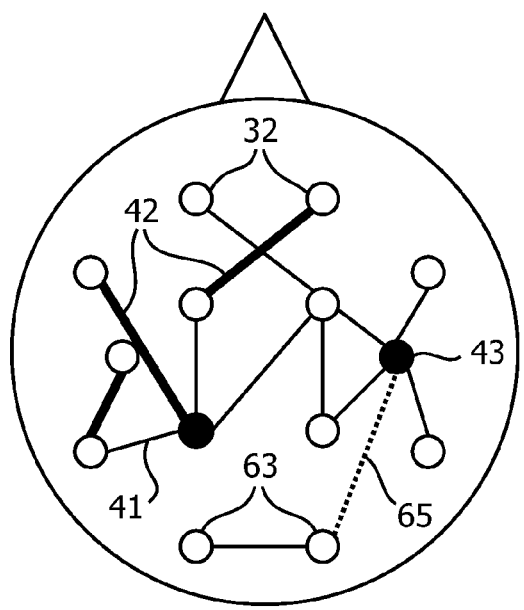

FIG. 6 visualizes a removal of a network connection 65 from the network of FIG. 4. The removal is indicated by using a dotted line 65, but may be indicated in different ways. As a result of this removal, two network sites 63 will lose the most important connection 65 to the functional network. This may cause temporary or permanent function loss.

Figure 7:
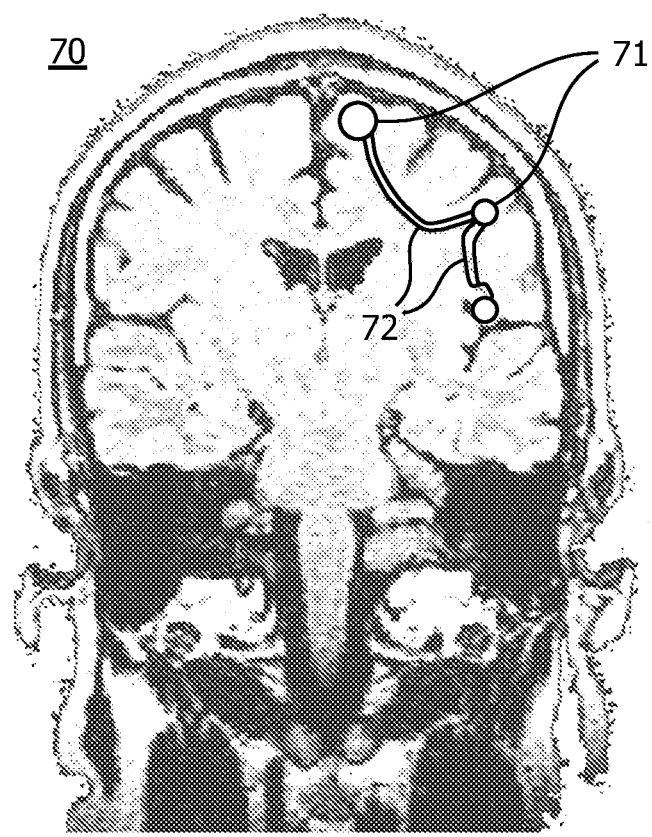
FIG. 7 shows an exemplary combination of anatomical and functional data according to the invention.

FIG. 7 shows an exemplary combination of anatomical and functional data according to the invention. The combined image 70 may be displayed on the display 14 of the neurosurgical planning system 10. The combined image 70 comprises an anatomical image of a cross section of the patient's brain and an overlay of the functional network. The overlay shows network sites 71 and fiber tracts 72 connecting theses network sites 71. More critical network sites are now drawn somewhat larger than the less important ones.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system (10) for planning a neurosurgical operation, the system (10) comprising:
    an input (11) for receiving functional data and anatomical data (25) of a brain region (31), and
    a processor (12) configured to:
    analyze the functional data (25) to form a network representation (27) of functional connections, the network representation (27) comprising network nodes (32) and network connections (41) interconnecting the network nodes (32),
    map the network representation (27) of the functional connections and the anatomical data to a common coordinate system,
    determine an expected function loss associated with a simulated removal of one of the network nodes (32) or network connections (41) from the network representation corresponding to a simulated intervention, and to
    identify at least one of: critical network connections and critical network nodes based on the expected function loss.

2. A system (10) for planning a neurosurgical operation as claimed in claim 1, wherein the processor (12) is further configured to perform a topological network analysis of the network representation (27) for determining the expected function loss.

3. A system (10) for planning a neurosurgical operation as claimed in claim 2, wherein the processor (12) is further configured to calculate at least one of: clustering coefficients of the network nodes (32) and path lengths of the network connections (41) for performing the topological network analysis of the network representation.

4. A system (10) for planning a neurosurgical operation as claimed in claim 1, wherein the functional data comprises multiple data channels (25) and wherein the processor (12) is further configured to calculate a pair wise correlation of the functional data channels (25) for analyzing the functional data.

5. A system (10) for planning a neurosurgical operation as claimed in claim 1, the system (10) further comprising planning tools for planning a surgical trajectory avoiding at least one of: the identified critical network connections and critical network nodes.

6. A system (10) for planning a neurosurgical operation as claimed in claim 1, further comprising an output (14) for providing a visual representation (29) of the network representation (27) of the functional connections.

7. A system (10) for planning a neurosurgical operation as claimed in claim 6, wherein at least one of: the critical network connections and the critical network nodes are highlighted in the visual representation (29).

8. A system (10) for planning a neurosurgical operation as claimed in claim 6, wherein an appearance of the network connections (41) and of the network nodes (32) in the visual representation (29) is dependent on the expected function loss.

9. A system (10) for planning a neurosurgical operation as claimed in claim 6, wherein the visual representation (29) further represents the anatomic data.

10. A system (10) for planning a neurosurgical operation as claimed in claim 6, wherein the functional data (25) comprises at least one of: fMRI, EEG, MEG and NIRS data.

11. A system (10) for planning a neurosurgical operation as claimed in claim 6, wherein the anatomic information comprises at least one of: MRI and DTI data.

12. A method (20) for planning a neurosurgical operation, the method comprising:
    receiving functional data (25) and anatomical data of a brain region (31),
    analyzing (26) the functional data (25) to form (22) a network representation (27) of functional connections, the network representation (27) comprising network nodes (32) and network connections (41) interconnecting the network nodes (32),
    mapping (24) the network representation (27) of the functional connections and the anatomical data to a common coordinate system,
    determining (23) an expected function loss associated with a simulated removal of one of the network nodes (32) or network connections (41) from the network representation (27) corresponding to a simulated intervention,
    based on the expected function loss, identifying at least one of: critical network connections and critical network nodes.

13. A computer program product for planning a neurosurgical operation, which program product comprises a non-transitory storage device having encoded thereon a program which is operative to cause a processor to perform the method as claimed in claim 12.

14. A system (10) for planning a neurosurgical operation as claimed in claim 1, wherein the functional data (25) comprises data linking neuronal activity to brain functions.

15. A system (10) for planning a neurosurgical operation as claimed in claim 1, wherein the functional data (25) comprises data showing correlation between neuronal activity in different parts of a nervous system.

* * * * *